(12) United States Patent
Treston et al.

(10) Patent No.: US 7,812,169 B2
(45) Date of Patent: Oct. 12, 2010

(54) METHOD OF SYNTHESIS OF 4-AMINO-THALIDOMIDE ENANTIOMERS

(75) Inventors: Anthony Treston, Rockville, MD (US); Jamshed H. Shah, Columbia, MD (US); Robert J. D'Amato, Lexington, MA (US); Kimberly A. Hunsucker, Alpharetta, GA (US); John Rougas, Westchester, PA (US); Barry P. Conner, Laurel, MD (US); Victor Pribdula, Silver Spring, MD (US); Glenn M. Swartz, Mt. Airy, MD (US)

(73) Assignee: The Children's Medical Center Corporation, Boston, MA (US)

( * ) Notice: Subject to any disclaimer, the term of this patent is extended or adjusted under 35 U.S.C. 154(b) by 1980 days.

(21) Appl. No.: 10/433,380

(22) PCT Filed: Nov. 30, 2001

(86) PCT No.: PCT/US01/45229

§ 371 (c)(1),
(2), (4) Date: Mar. 11, 2004

(87) PCT Pub. No.: WO02/064083

PCT Pub. Date: Aug. 22, 2002

(65) Prior Publication Data

US 2004/0147558 A1    Jul. 29, 2004

Related U.S. Application Data

(60) Provisional application No. 60/250,219, filed on Nov. 30, 2000.

(51) Int. Cl.
*C07D 401/06*    (2006.01)
(52) U.S. Cl. ..................................... 546/201
(58) Field of Classification Search .................. 546/201
See application file for complete search history.

(56) References Cited

U.S. PATENT DOCUMENTS

| | | | |
|---|---|---|---|
| 2,830,991 A | 4/1958 | Keller et al. |
| 3,536,809 A | 10/1970 | Applezweig |
| 3,560,495 A | 2/1971 | Frankus et al. |
| 3,563,986 A | 2/1971 | Frankus et al. |
| 3,598,123 A | 8/1971 | Zaffaroni et al. |
| 3,625,946 A | 12/1971 | Heinrich et al. |
| 3,705,162 A | 12/1972 | Graudums et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,552,888 A | 11/1985 | Koppel et al. |
| 4,810,643 A | 3/1989 | Souza |
| 4,994,443 A | 2/1991 | Folkman et al. |
| 4,999,291 A | 3/1991 | Souza |
| 5,001,116 A | 3/1991 | Folkman et al. |
| 5,021,404 A | 6/1991 | Folkman et al. |
| 5,059,595 A | 10/1991 | Le Grazie |
| 5,073,543 A | 12/1991 | Marshall et al. |
| 5,120,548 A | 6/1992 | McClelland et al. |
| 5,134,127 A | 7/1992 | Stella et al. |
| 5,229,496 A | 7/1993 | Deeley et al. |
| 5,260,329 A | 11/1993 | Montegilli et al. |
| 5,354,556 A | 10/1994 | Sparks et al. |
| 5,385,901 A | 1/1995 | Kaplan et al. |
| 5,391,485 A | 2/1995 | Deeley et al. |
| 5,393,870 A | 2/1995 | Deeley et al. |
| 5,399,363 A | 3/1995 | Liversidge et al. |
| 5,405,855 A | 4/1995 | Andrulis, Jr. |
| 5,434,170 A | 7/1995 | Andrulis, Jr. |
| 5,443,824 A | 8/1995 | Piacquadio |
| 5,502,066 A | 3/1996 | Heinemann et al. |
| 5,528,823 A | 6/1996 | Rudy, Jr. et al. |
| 5,580,755 A | 12/1996 | Souza |
| 5,591,767 A | 1/1997 | Mohr et al. |
| 5,593,990 A | 1/1997 | D'Amato |
| 5,605,684 A | 2/1997 | Piacquadio |
| 5,605,914 A | 2/1997 | Muller |
| 5,629,327 A | 5/1997 | D'Amato |
| 5,635,517 A | 6/1997 | Muller et al. |
| 5,639,476 A | 6/1997 | Oshlack et al. |
| 5,639,725 A | 6/1997 | O'Reilly et al. |

(Continued)

FOREIGN PATENT DOCUMENTS

EP    0325199    7/1989

(Continued)

OTHER PUBLICATIONS

C. Bonzano, European Communication pursuant to Article 96(2) EPC in connection with EP Application No. 01270117.3-1216, dated Jul. 12, 2005.

(Continued)

*Primary Examiner*—James O Wilson
*Assistant Examiner*—Ebenezer Sackey
(74) *Attorney, Agent, or Firm*—Jones Day

(57) ABSTRACT

The invention provides new and useful analogs of 4-amino-thalidomide. These analogs include S(−)-4-amino-thalidomide and R(+)-4-amino-thalidomide. The invention also provides processes for making these analogs. Further, the invention provides methods for inhibiting angiogenesis and treating angiogenesis-associated diseases, including cancer and macular degeneration, by administering these compounds.

4 Claims, 2 Drawing Sheets

U.S. PATENT DOCUMENTS

| | | | |
|---|---|---|---|
| 5,643,915 A | 7/1997 | Andrulis, Jr. et al. |
| 5,654,312 A | 8/1997 | Andrulis, Jr. et al. |
| 5,674,533 A | 10/1997 | Santus et al. |
| 5,679,696 A | 10/1997 | Fenton et al. |
| 5,698,579 A | 12/1997 | Muller |
| 5,712,291 A | 1/1998 | D'Amato |
| 5,731,325 A | 3/1998 | Andrulis, Jr. et al. |
| 5,733,566 A | 3/1998 | Lewis |
| 5,733,876 A | 3/1998 | O'Reilly et al. |
| 5,776,704 A | 7/1998 | O'Reilly et al. |
| 5,792,845 A | 8/1998 | O'Reilly et al. |
| 5,798,368 A | 8/1998 | Muller et al. |
| 5,837,682 A | 11/1998 | Folkman et al. |
| 5,854,205 A | 12/1998 | O'Reilly et al. |
| 5,854,221 A | 12/1998 | Cao et al. |
| 5,861,372 A | 1/1999 | Folkman et al. |
| 5,874,448 A | 2/1999 | Muller et al. |
| 5,877,200 A | 3/1999 | Muller |
| 5,885,795 A | 3/1999 | O'Reilly et al. |
| 5,929,117 A | 7/1999 | Muller et al. |
| 5,948,403 A | 9/1999 | Sone et al. |
| 5,955,476 A | 9/1999 | Muller et al. |
| 6,020,358 A | 2/2000 | Muller et al. |
| 6,071,948 A | 6/2000 | D'Amato |
| 6,114,355 A | 9/2000 | D'Amato |
| 6,140,346 A | 10/2000 | Andrulis, Jr. et al. |
| 6,228,879 B1 | 5/2001 | Green et al. |
| 6,235,756 B1 | 5/2001 | D'Amato |
| 6,281,230 B1 | 8/2001 | Muller et al. |
| 6,316,471 B1 * | 11/2001 | Muller et al. ............... 514/323 |
| 6,326,388 B1 | 12/2001 | Man et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,420,414 B1 | 7/2002 | D'Amato |
| 6,458,810 B1 | 10/2002 | Muller et al. |
| 6,469,045 B1 | 10/2002 | D'Amato |
| 6,476,052 B1 | 11/2002 | Muller et al. |
| 6,518,298 B2 | 2/2003 | Green et al. |
| 6,555,554 B2 | 4/2003 | Muller et al. |
| 7,153,867 B2 * | 12/2006 | Shah et al. ............... 514/323 |
| 2001/0018445 A1 | 8/2001 | Huang et al. |
| 2001/0056114 A1 | 12/2001 | D'Amato |
| 2002/0035090 A1 | 3/2002 | Zeldis et al. |
| 2002/0045643 A1 | 4/2002 | Muller et al. |
| 2002/0049231 A1 | 4/2002 | D'Amato |
| 2002/0052398 A1 | 5/2002 | D'Amato |
| 2002/0054899 A1 | 5/2002 | Zeldis |
| 2002/0061923 A1 | 5/2002 | D'Amato |
| 2002/0082290 A1 | 6/2002 | D'Amato |
| 2002/0128228 A1 | 9/2002 | Hwu |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0013739 A1 | 1/2003 | Masferrer et al. |
| 2003/0028028 A1 | 2/2003 | Man et al. |
| 2003/0045552 A1 | 3/2003 | Robarge et al. |
| 2003/0069428 A1 | 4/2003 | Muller et al. |
| 2003/0096841 A1 | 5/2003 | Robarge et al. |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0187024 A1 | 10/2003 | D'Amato |
| 2003/0191098 A1 | 10/2003 | D'Amato |
| 2003/0235909 A1 | 12/2003 | Hariri et al. |
| 2004/0029832 A1 | 2/2004 | Zeldis |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |
| 2004/0127545 A1 | 7/2004 | D'Amato et al. |
| 2004/0220144 A1 | 11/2004 | Zeldis |
| 2004/0266809 A1 | 12/2004 | Emanuel et al. |
| 2005/0096351 A1 | 5/2005 | Jaworsky et al. |
| 2005/0203142 A1 | 9/2005 | Zeldis et al. |

FOREIGN PATENT DOCUMENTS

| | | |
|---|---|---|
| EP | 0357061 | 3/1990 |
| GB | 768821 | 2/1957 |
| JP | 58-131978 | 8/1983 |
| JP | 63-119500 | 5/1988 |
| WO | WO 91/10424 | 7/1991 |
| WO | WO 92/14455 | 9/1992 |
| WO | WO 92/18496 | 10/1992 |
| WO | WO 94/20085 | 9/1994 |
| WO | WO 95/04533 | 2/1995 |
| WO | WO 98/03502 | 1/1998 |
| WO | WO 98/54170 | 12/1998 |
| WO | WO 00/55134 | 9/2000 |
| WO | WO 01/70275 | 9/2001 |
| WO | WO 01/87307 | 11/2001 |
| WO | WO 02/059106 | 8/2002 |
| WO | WO 02/064083 | 8/2002 |
| WO | WO 03/086373 | 10/2003 |

OTHER PUBLICATIONS

Polonski, "Circular Dichroism Spectra and Molecular Geometry of Six-Membered Ring Anhydrides and Imides," *J. Chem. Soc., Perkin Trans. 1*, 1988, pp. 639-648.

Matsumura et al., "New Reaction Conditions Using Trifluoroethanol for the E-I Hofmann Rearrangement," *J. Chem. Soc., Perkin Trans. 1*, 1999, pp. 2057-2060.

Lee et al., "The Effect of N-Substituted Alkyl Groups on Anticonvulsant Activities of N-Cbz-a-amino-N-alkylglutarimides," Arch. Pharm. Res., vol. 22, No. 5, pp. 491-495 (1999).

U.S. Appl. No. 09/287,377, filed Apr. 7, 1999, D'Amato.

Corral et al., 1999, "Immunomodulation Immunomodulation by thalidomide and thalidomide analogues," Ann Rheum Dis. Suppl 1:1107-13.

D'Amato et al., 2001, "Mechanism of action of thalidomide and 3-aminothalidomide in multiple myeloma," Semin. Oncol. 28:597-601.

He, W. et al., 1993, 206th American Chemical Society, Chicago, IL; Med. Chem., paper 216.

Jonsson, 1972, "Chemical structure and teratogenic properties. 3. A review of available data on structure-activity relationships and mechanism of action of thalidomide analogues," Acta. Pharm. Suec. 9(6):521-542.

Lentzsch et al., 2002, "S-3-amino-phthalimido-glutarimide inhibits angiogenesis and growth of B-cell neoplasias in mice," Cancer Research 62:2300-2305.

Muller et al., 1999, "Amino-substituted thalidomide analogs; potent inhibitors of TNF-alpha production," Bioorg. Med. Chem. Lett. 9(11):1625-1630.

Shah et al., 1999, "Synthesis and enantiomeric separation of 2-phthalimidino-glutaric acid analogues: potent inhibitors of tumor metastasis," J. Med. Chem. 42:3014-3017.

Wilen et al., 1977, "Tetrahedron Report No. 38 Strategies in optical resolutions," Tetrahedron 33:2725-2736.

Wilen, 1972, Tables of Resolving Agents and Optical Resolutions, E.L. Eliel, ed., Univ. of Notre Dame Press, Notre Dame, IN pp. 268-298.

Wolff, 1995, Burger's Medicinal Chemistry and Drug Discovery, 5th ed., pp. 172-178, 950-982.

* cited by examiner

US 7,812,169 B2

METHOD OF SYNTHESIS OF 4-AMINO-THALIDOMIDE ENANTIOMERS

This application is a U.S. national stage under 35 U.S.C. §371 of International Application No. PCT/US01/45229, filed Nov. 30, 2001, which claims the benefit of U.S. Provisional Patent Application No. 60/250,219, filed Nov. 30, 2000.

TECHNICAL FIELD

The present invention relates to methods of preparing enantiomers of 4-amino-thalidomide and compositions for preventing unwanted angiogenesis in a human or animal. More particularly, the present invention relates to a method for preventing unwanted angiogenesis, particularly in angiogenesis dependent or associated diseases, by administration of enantiomers of 4-amino-thalidomide.

BACKGROUND OF THE INVENTION

Angiogenesis is the generation of new blood vessels into a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic-associated diseases.

One example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens disease, acne rosacea, phylectenulosis, syphilis, Mycobacteria infections, lipid degeneration, chemical burns, bacterial ulcers, fungal ulcers, *Herpes simplex* infection, *Herpes zoster* infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Diseases associated with retinalchoroidal neovascularization include, but are not limited to, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other eye-related diseases include, but are not limited to, diseases associated with rubeosis (neovascularization of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the bone destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels and the inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J. Med.*, 285:1182-86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

The growth rate of tumors implanted in subcutaneous transparent chambers in mice is slow and linear before neovascularization, and rapid and nearly exponential after neovascularization. (Algire, et al., *J. Nat. Cancer Inst.*, 6:73-85 (1945)).

Tumors grown in isolated perfused organs where blood vessels do not proliferate are limited to 1-2 mm$^3$ but expand rapidly to >1000 times this volume when they are transplanted to mice and become neovascularized. (Folkman, et al., *Annals of Surgery*, 164:491-502 (1966)).

Tumor growth in the avascular cornea proceeds slowly and at a linear rate, but switches to exponential growth after neovascularization. (Gimbrone, Jr., et al., *J. Nat. Cancer Inst.*, 52:421-27 (1974)).

Tumors suspended in the aqueous fluid of the anterior chamber of the rabbit eye remain viable, avascular, and limited in size to <1 mm$^3$. Once they are implanted on the iris vascular bed, they become neovascularized and grow rapidly, reaching 16,000 times their original volume within 2 weeks. (Gimbrone, Jr., et al., *J. Exp. Med.*, 136:261-76).

When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer*, 35:347-56 (1977)).

Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery*, 68:334-40 (1970)).

In transgenic mice which develop carcinomas in the beta cells of the pancreatic islets, pre-vascular hyperplastic islets are limited in size to <1 mm. At 6-7 weeks of age, 4-10% of the islets become neovascularized, and from these islets arise large vascularized tumors of more than 1000 times the volume of the pre-vascular islets. (Folkman, et al., *Nature*, 339:58-61 (1989)).

A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim, et al., *Nature*, 362:841-44 (1993)).

Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.*, 51:6180-84 (1991)).

Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross, et al., *Proc. Am. Assoc. Cancer Res.*, 31:79 (1990)).

A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature*, 48:555-57 (1990)). There is also indirect clinical evidence that tumor growth is angiogenesis dependent.

Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

Carcinoma of the ovary metastasizes to the peritoneal membrane as tiny avascular white seeds (1-3 mm$^3$). These implants rarely grow larger until one or more of them becomes neovascularized.

Intensity of neovascularization in breast cancer (Weidner, et al., *New Eng. J. Med.*, 324:1-8 (1991); Weidner, et al., *J Nat. Cancer Inst.*, 84:1875-87 (1992)) and in prostate cancer (Weidner, et al., *Am. J. Pathol.*, 143(2):401-09 (1993)) correlates highly with risk of future metastasis.

Metastasis from human cutaneous melanoma is rare prior to neovascularization. The onset of neovascularization leads to increased thickness of the lesion and an increased risk of metastasis. (Srivastava, et al., *Am. J. Pathol.*, 133:419-23 (1988)).

In bladder cancer, the urinary level of an angiogenic protein, bFGF, is a more sensitive indicator of status and extent of disease than is cytology. (Nguyen, et al., *J. Nat. Cancer Inst.*, 85:241-42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, lymphomas, multiple myeloma, and any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukemia and lymphoma tumors and multiple myeloma diseases.

One of the most frequent angiogenic diseases of childhood is the hemangioma. A hemangioma is a tumor composed of newly-formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatitic arteriovenous fistula.

What is needed, therefore, is a composition and method which can inhibit angiogenesis. What is also needed is a composition and method which can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogenesis. Taylor, et al. (*Nature*, 297:307 (1982)) have used protamine to inhibit angiogenesis. The toxicity of protamine limits its practical use as a therapeutic. Folkman, et al. (*Science*, 221:719 (1983), and U.S. Pat. Nos. 5,001,116 and 4,994,443) have disclosed the use of heparin and steroids to control angiogenesis. Steroids, such as tetrahydrocortisol, which lack gluccocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogenesis in mouse dermis stimulated by human neoplastic cells. Interferon beta is also a potent inhibitor of angiogenesis induced by allogeneic spleen cells. (Sidky, et al., *Cancer Res.*, 47:5155-61(1987)). Human recombinant interferon (alpha/A) was reported to be successfully used in the treatment of pulmonary hemangiomatosis, an angiogenesis-induced disease. (White, et al., *New Eng. J. Med.*, 320:1197-1200 (1989)).

Other agents which have been used to inhibit angiogenesis include ascorbic acid ethers and related compounds. (Japanese Kokai Tokkyo Koho No.58-13 (1978)). Sulfated polysaccharide DS 4152 also inhibits angiogenesis. (Japanese Kokai Tokkyo Koho No. 63-119500). Additional anti-angiogenic compounds include Angiostatin® (U.S. Pat. Nos. 5,639,725; 5,792,845; 5,885,795; 5,733,876; 5,776,704; 5,837,682; 5,861,372, and 5,854,221) and Endostatin™ (U.S. Pat. No. 5,854,205).

Another compound which has been shown to inhibit angiogenesis is thalidomide. (D'Amato, et al., *Proc. Natl. Acad. Sci.*, 90:4082-85 (1994)). Thalidomide is a hypnosedative that has been successfully used to treat a number of angiogenesis-associated diseases, such as rheumatoid arthritis (Gutierrez-Rodriguez, *Arthritis Rheum.*, 27 (10):1118-21 (1984); Gutierrez-Rodriguez, et al., *J. Rheumatol.*, 16(2): 158-63 (1989)), Behcet's disease (Handley, et al, *Br. J. Dermatol.*, 127 Suppl, 40:67-8 (1992); Gunzler, *Med. Hypotheses*, 30(2):105-9 (1989)), graft versus host rejection (Field, et al., *Nature*, 211(55): 1308-10 (1966); Heney, et al., *Br. J. Haematol.*, 78 (1):23-7 (1991)), Mycobacteria diseases (Vicente, et al., *Arch. Intern. Med.*, 153(4):534 (1993)), *Herpes simplex* and *Herpes zoster* infections (Naafs, et al., *Int. J. Dermatol.*, 24(2):131-4 (1985)), chronic inflammation, ulcerative colitis (Meza, et al., *Drug Ther*, 23 (11): 74-80, 83 (1993); Powell, et al., *Br. J. Dermatol.*, 113 Suppl 28: 141-4 (1985)), leprosy (Barnes, et al., *Infect. Immun.*, 60(4):1441-46 (1992)) and lupus (Burrows, *BMJ*, 307: 939-40 (1993)).

Although thalidomide has minimal side effects in adults, it is a potent teratogen. Thus, there are concerns regarding its use in women of child-bearing age. Although minimal, there are a number of side effects which limit the desirability of thalidomide as a treatment. One such side effect is drowsiness. In a number of therapeutic studies, the initial dosage of thalidomide had to be reduced because patients became lethargic and had difficulty functioning normally. Another side effect limiting the use of thalidomide is peripheral neuropathy, in which individuals suffer from numbness and disfunction in their extremities.

Thus, improved methods and compositions are needed that are easily administered and capable of inhibiting angiogenesis.

SUMMARY OF THE INVENTION

The present invention provides new derivatives to 4-amino-thalidomide which are analogs of thalidomide. Specifically, the present invention provides for the individual R(+) and S(−) enantiomers of 4-amino-thalidomide and processes for preparing these enantiomers.

The enantiomers of the present invention have the following structures:

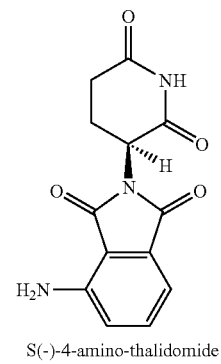

S(−)-4-amino-thalidomide

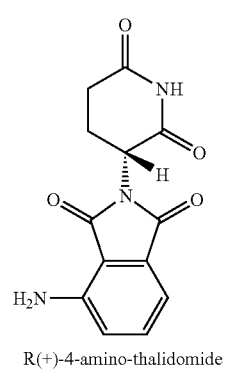

R(+)-4-amino-thalidomide

In another aspect of the present invention, compositions and methods are provided that are effective in inhibiting abnormal mitosis and/or unwanted angiogenesis. These compositions are easily administered by different routes including oral and can be given in dosages that are safe and provide mitotic and/or angiogenic inhibition at internal sites. The present invention provides a method of treating mammalian diseases mediated by undesired and uncontrolled mitosis and/or angiogenesis by administering a composition comprising an anti-mitotic and/or anti-angiogenic compound in a dosage sufficient to inhibit angiogenesis.

Other features and advantages of the invention will be apparent from the following description of preferred embodiments thereof.

These and other objects, features and advantages of the present invention will become apparent after a review of the following detailed description of the disclosed embodiments and the appended claims.

DETAILED DESCRIPTION OF THE INVENTION

Figure 1:
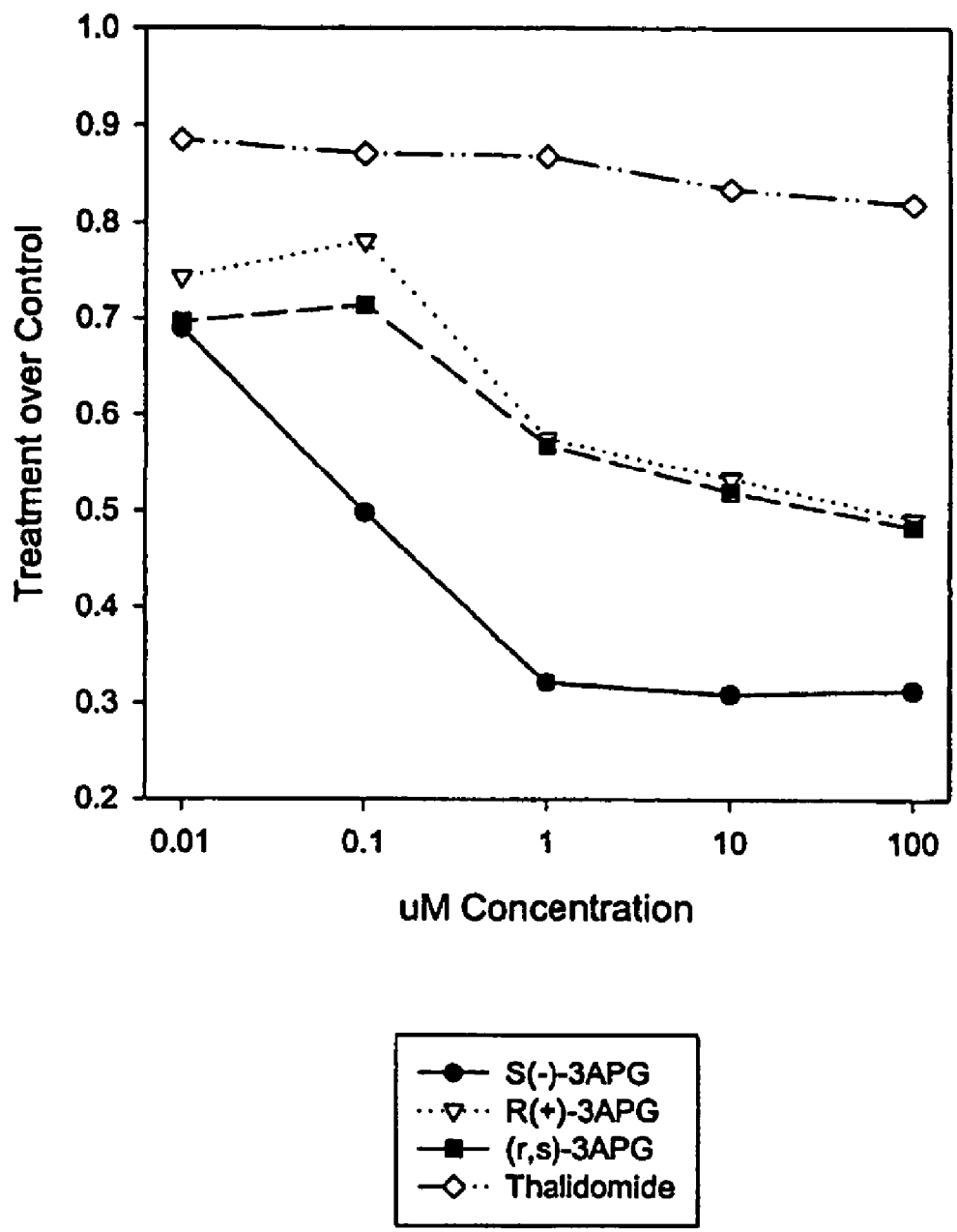
FIG. 1 illustrates the results of XTT proliferation with HS-Sultan cells.

The present invention is directed to compositions and methods for the treatment of diseases that are mediated by abnormal mitosis and/or angiogenesis. As described below, compounds employed in the present invention exhibit anti-mitotic, antiangiogenic, and/or anti-tumor properties. Further, in accordance with the present invention, a method is provided to synthesize substantially enantiomerically pure S(−)-4-amino-thalidomide and R(+)-4-aminothalidomide. In accordance with the present invention, S(−) and R(+) enantiomers of 4-amino-thalidomide have anti-mitotic and angiogensis inhibitory activities and are useful for the treatment of a number of diseases, including various cancers and macular degeneration. S(−)-4-amino-thalidomide showed potent anti-angiogenic and anti-tumor activity in various in-vito and in-vivo tumor models.

The enantiomers of the present invention have the following structures:

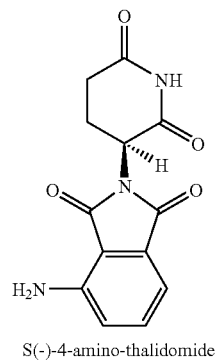

S(−)-4-amino-thalidomide

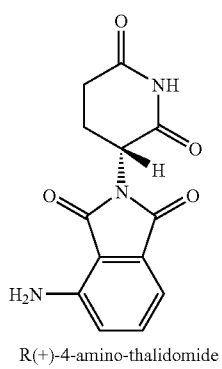

R(+)-4-amino-thalidomide

In one aspect of the present invention, S(−)4-amino-thalidomide and R(+)-4-amino-thalidomide may be synthesized from S(−) and R(+) enantiomers of 4-nitro-thalidomide, respectively. For example, S(−)-4-amino-thalidomide may be produced in accordance with the following reaction scheme:

Synthesis of S(-)-4-amino-thalidome

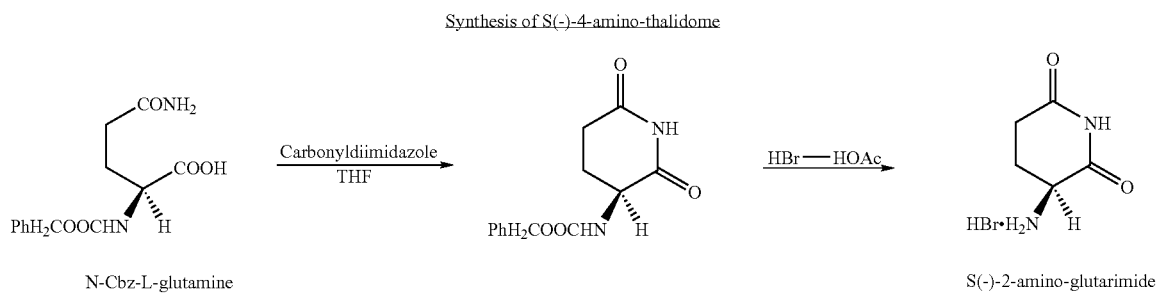

N-Cbz-L-glutamine

S(-)-2-amino-glutarimide

-continued

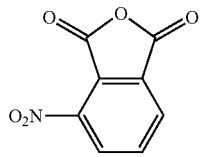

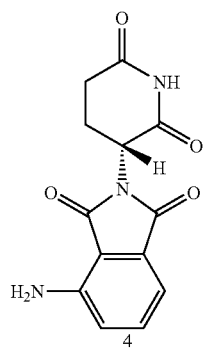

Pd—C 5%
H₂/Dioxane/MeOH

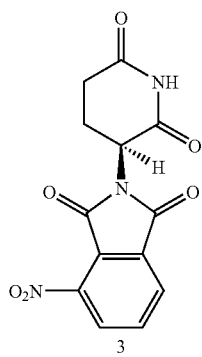

HOAc/
DMF
70-80° C.
18 h

4
S(-)-4-amino-thalidomide

3
S(-)-4-nitro-thalidomide

The S(-)- and R(+) enantiomers of 4-amino-thalidomide can be provided as pharmaceutically and physiologically acceptable formulations using methods and techniques known to those of ordinary skill in the art. These formulations can be administered by standard routes. In general, the combinations may be administered by the topical, transdermal, oral, rectal or parenteral (e.g., intravenous, subcutaneous, or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441-446 (1991).

The dosage of the compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 0.1 to 2 mg/kg/day, is generally sufficient.

The formulations include those suitable for oral, rectal, nasal, ophthalmic (including intravitreal or intracameral), topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams, or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

The present invention can be used to treat diseases characterized by abnormal cell mitosis. Further, the present invention may be employed to treat any disease characterized by angiogensis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyrogenic granulomas, vascular malfunctions, abnormal wound healing, inflammatory and immune disorders, Bechet's disease, gout or gouty arthritis, abnormal angiogenesis accompanying: rheumatoid arthritis, skin diseases, such as psoriasis, diabetic retinopathy, and other ocular angiogenic diseases such as retinopathy of prematurity (retrolental fibroplasic), macular degeneration, corneal graft rejection, neuroscular glaucoma, liver diseases and Oster Webber syndrome (Osler-Weber Rendu disease).

Diseases associated with corneal neovascularization that can be treated according to the present invention include but are not limited to, diabetic retinopathy, retinopathy of prematurity, corneal graft rejection, neovascular glaucoma and retrolental ibroplasias, epidemic keratoconjunctivitis, Vitamin A deficiency, contact lens overwear, atopic keratitis, superior limbic keratitis, pterygium keratitis sicca, Sjogren's syndrome, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Steven-Johnson disease, pemphigoid radial keratotomy, and corneal graft rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhagic telangiectasia, solid or blood borne tumors and acquired immune deficiency syndrome.

Studies of the S(−)- and R(+) enantiomers of 4-aminothalidomide, particulary S(−)-4-aminothalidomide, show that these compounds are as potent as inhibitors of angiogenesis. These studies indicate that these compounds are useful for the treatment of angiogenesis-associated diseases. As indicated above, one angiogenesis-associated group of diseases is cancer. Numerous tumors, including solid tumors and blood-borne tumors, require angiogenesis to grow beyond a very small size. Inhibition of angiogenesis will result in inhibition of growth of the tumor. Examples of specific types of cancer which can be treated with the S(−)- and R(+) enantiomers of 4-amino-thalidomide include, but are not limited to, prostate cancer, breast cancer, cervical cancer, uterine cancer, ovarian cancer, gliomas, hemangiomas, Kaposi's sarcoma, pancreatic cancer, retinoblastomas, melanomas, bladder cancer, rhabdomyosarcomas, retinoblastomas, Ewing's sarcoma, neuroblastomas, osteosarcoma, leukemias, lymphomas, multiple myeloma, and various acute and chronic neoplastic diseases of the bone marrow. The S(−)- and R(+) enantiomers of 4-aminothalidomide also inhibit metastases of existing tumors. Examples of metastases which can be inhibited include, but are not limited to, bone metastases, lung metastases, liver metastases, and peritoneal metastases.

This invention is further illustrated by the following examples, which are not to be construed in any way as imposing limitations upon the scope thereof On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The table below provides desired embodiments, while the Examples provide the synthesis of representative compounds.

EXAMPLES

The following compounds were synthesized by modification in methods described in Shealy, et al. *J. Pharm. Sci.*, 1968, 57, 757-764; Polonski, et al. *J. Chem. Soc. Perkin Trans. I*, 1988, 639-648; Muller, et al. *Bioorg. Med. Chem. Lett.*, 1999, 9, 1625-1630; Helm, et al. *Arzneim-Forsch./Drug*

Res., 1981, 31, 941-949; Shah, et al., *J. Med. Chem.*, 1999, 42, 3014-3017; and Menard, et al., *Can. J. Che.,* 1963, 41, 1722-1725.

Example 1

Synthesis of S(−)-(3-benzyloxycarbonylamino)-glutamide

Into a stirring solution of carboxybenzyloxy-L-glutamine (2.8 g, 10 mmols) in 40 mL anhydrous THF (tetrahydrofuiran), 1,1-carbonyldiimidazole (1.92 g, 12 mmols) were added. The reaction mixture was heated under reflux for 18 hours. The THF was evaporated and the product was dissolved in chloroform. The chloroform layer was washed with water and brine and dried over anhydrous $CaSO_4$, filtered and evaporated to give white solid. The solid product was crystallized from ethyl ether to give 2.4 grams crystalline powder (90%). (Alternatively, carboxybenzyloxy-L-glutamine can be cyclized by treating with $SOCl_2$ in DMF (N,N-dimethylformamide) at −70° C. to 0° C. for 1 hour to form S(−)-(3-benzyloxycarbonylamino)-glutarimide. The reaction mixture was diluted with $CHCl_3$ and washed with 5% $Na_2CO_3$, dried over anhydrous $Na_2SO_4$, filtered, and evaporated to give 2.5 g (90% yield) S(−)-(3-benzyloxycarbonylamino)-glutarimide).

1H NMR in $CDCl_3$ confirmed the product as S(−)-(3-benzyloxycarbonylamino)-glutarimide). 1H NMR ($CDCL_3$, PPM), 8.2 (1H, s broad), 7.4 (5H, s, aromatic), 5.8 (1H, d), 5.15 (2H, s), 4.4 (1H, dd, J=4.5, 3), 2.95-2.4 (3H, m), 1.86 (1H, d, t, J=11.5, 6.5). m. p. 122-124° C. (lit=122-124° C.).

Example 2

Synthesis of S(−)-3-Amino-glutarimide.HBr

Into a solution of S(−)-(2-benzyloxycarbonylamino)glutarimide (1.2 g, 4.6 mmols) in 15 mL acetic acid glacial, 8 mL of 30% HBr/ acetic acid solution was added at 20° C. The temperature of reaction mixture was raised to RT and stirred for 1 hour. White solid powder of S-(−)-2-amino-glutarimide.HBr started appearing in reaction mixture. The solid was filtered and washed with 5 mL acetic acid glacial and then with ether to give 1.8 g (80%) product. Analysis on polarimeter of product showed (−) rotation, $[a]^{25}_D$ (c=1, water)=−37.5° and confirmed the product as S-(−)-2-amino-glutarimide. 1H NMR in DMSO-D6 confirmed the product as 2-amino-L-glutarimide.HBr.

Example 3

Synthesis of S(−)-3-Nitro-thalidonide

Into a solution of (4.18 g, 20 mmols S-(−)-2-amino-glutarimide.HBr in 50 mL of anhydrous DMF, 3.8 g (20 mmols) of 3-nitrophthalic anhydride was added. After adding 100 mL acetic acid (glacial), the reaction mixture was heated at about 70° C. to about 80° C. for about 24 hours. Thereafter, the solvents were evaporated under vacuum to yield an off-white solid. On adding 10 mL ethyl alcohol to the solid, an off-white powder product was formed. The product was separated and washed with 20 mL ethyl alcohol.

1H NMR in DMSO-D6 confirmed the product as S(−)-3-nitro-tholidomide. m. p. 228-229° C. (lit=228.5-229.5° C.). 1H NMR (DMSO-$D_6$, PPM),11.25 (1H, s broad), 8.35 (1H, d, J=7.2), 8.25 (1H, d, J=7.0), 8.15 (1H, t, J=8.0), 5.2 (1H, dd, J=5.5, 7.2), 3.00-2.85 (1H, m), 2.65-2.4 (2H, m), 2.15-2.05 (1H, m).

Example 4

Synthesis of S(−)4-Amino-thalidomide:

4-Nitro-thalidomide (1 g, 3.3 mmols) was dissolved in 50 mL dioxane/methanol 4:1 mixture and hydrogenated in a Parr hydrogenater at 40 psi of hydrogen in the presence of a Pd/C 5% catalyst for about 4 hours. After filtering the reaction mixture through a Celite filtering agent, the solvents were evaporated under vacuum to yield a yellow powder. The product was recrystallized from ethyl acetate/dioxane to yield 800 mg (85% purity) of S(−)-4-amino-thalidomide.

1H NMR in DMSO-$D_6$ confirmed the product as S(−)-4-amino-thalidomide. m.p. 318.2-319.5° C. 1H NMR (DMSO-$D_6$, PPM), 11.10 (1H, s broad), 7.45 (1H, t, J=7. 5), 7.05 (1H, d, J=5.2), 6.95 (1H, d, J=5.2), 6.5 (2H, s broad), 5.05 (1H, dd, J=5.0, 13.42),2.95-2.80 (1H, m), 2.65-2.5 (2H, m), 2.05-1.95 (1H, m). Absolute configuration was determined by comparison of specific rotation $[a]^{25}_D$ of R- and S-4amino-thalidomide to the analogous compounds R(+)- and S(−)-thalidomide. Analysis on polarimeter of product showed (−) rotation, $[a]^{25}_D$ (C=0.5, dioxane) =-27.70° and confirmed the product as S(−)-4-amino-thalidomide.

The two enantiomers of 4-amino-thalidomide were resolved by chiral HPLC column Welk-01 (10 mm×750 mm) and eluted with CH3CN/MeOH/H20 1:1:5 mixture. The retention time for the S(−) enantiomer was 33.74 minutes and for the R(+) enantiomer 35.62 minutes at a flow rate of 2 mL/min at 240 nm, respectively.

Example 5

Synthesis of R(+)-4amino-thalidomide:

Compound R(+)-4-amino-thalidomide was synthesized by the same procedure as for S(−)-4-amino-thalidomide above, except the synthesis was started with commercially available carboxybenzyloxy-D-glutamine, which formed R(+)-4-nitro-thalidomide (See Example 1). Analysis on polarimeter of product showed (+) rotation $[a]^{25}_D$ (c=1, dioxane)=+37.0° and confirmed the product as R(+)-4-amino-thalidomide. 1H NMR in DMSO-D6 confirmed the product as 4-amino-thalidomide.

Example 6

Synthesis of S(−)-Amino-thalidomide:

S(−)-4-Amino-thalidomide may be synthesized by dissolving S(−)-4-nitro-thalidomide in concentrated HCl and then treating the reaction mixture with granulated tin. After heating the reaction mixture at about 70° C. to about 80° C. for about 2 hours, the reaction mixture should be filtered and the acid evaporated under vacuum to yield a yellow powder. The product should be recryrstallized from water and then ethyl acetate/dioxane to yield S(−)-4-amino-thalidomide.

Example 7

The Roche Cell Proliferation Kit II (XTT) is an useful assay for screening the relative efficacy of small molecules. The assay quantitatively determines cellular proliferation in response to agonists and/or antagonists of proliferation. It is based on the cleavage of the yellow tetrazolium salt (XTT) by metabolically active/viable cells to form an orange formazan dye. The formation of the soluble dye allows direct quantification using a scanning mulitwell spectrophotometer. An increase in the number of living cells (resulting from proliferation) results in a greater production of formazan dye which corresponds to an increase in the absorbance value.

When evaluating analogs of thalidomide, or the like, we have employed HS-Sultan cells in an in vitro XTT assay. In each well of a 96-well microtiter plate, cells are seeded at a density of 15,000 cells per 90 µL of normal growth media approximately 16 hours prior to treatments. During culture and treatments, cells are maintained at 37° C. with 5% $CO_2$ in a high humidity incubator. Treatments (10×) are added in 10 µL aliquots to achieve a 1× final treatment concentration in each well. Each concentration is done in triplicate. The XTT labeling mixture is added in 50 µL aliquots to each well during the final four hours of the 72 hour treatment period. When the treatment/labeling period is complete, the plate is read on a spectrophotometric plate reader at a wavelength of 470 nm and a 650 nm reference wavelength. For individual experiments, the average absorbance values (with background subtracted) for each treatment are plotted against the concentration. A larger absorbance value corresponds to a greater amount of proliferation. A negative control (untreated cells) is used as a point of reference; an absorbance value less than the control reflects inhibition of proliferation.

When comparing experiments conducted over a period of time, absorbance values from each experiment may vary due to a number of factors (degradation of the XTT reagents over time is the most common factor). When using reagents from an older XTT kit or switching to a new kit, the overall absorbance values for that individual experiment may be higher or lower, making a direct comparison to another experiment difficult. Therefore, it is common practice to convert the absorbance values to a ratio of the treated values divided by the negative control value (treatment over control) when comparing the results from multiple experiments; the "treatment over control" values for each treatment are then plotted against the uM concentration. FIG. 1 compares the 4-amino-thalidomide enantiomers. The R and the R,S plots represent data pooled from 3 experiments. The S and thalidomide plots represent data pooled from about 12 experiments. As illustrated in FIG. 1, both the S(−)- and the R(+)-4-amino-thalidomide enantiomers show anti-cellular proliferation activity.

Example 8

Antitumor activity has been evaluated for the S(−) and the R(+)-4-amino-thalidomide enantiomers as follows. For the HsS cell line, 2 million cells are injected into the tail vein of 8 week old, female, SCID mice. Treatment is initiated after two weeks and continued daily until the mice die or show hind limb paralysis. Results are expressed as mean time to death in treated versus control animals. For the Lewis lung model, 2.5×10 (5) cells are injected intravenously into the tail vein of 6-8 week old, male, C57BL/6 mice and treatment is initiated on day three. The time period of treatment is usually 11-15 days in duration. After sacrifice by $CO_2$ asphyxiation, lungs (where tumors seed and grow) are removed, rinsed in water, patted dry, and weighed. Mean lung weights of age-matched, non-tumor bearing mice are subtracted from the weight of treated, tumor-bearing mice with results expressed as lung weight gain in treated versus control animals. Table 1 summarizes data from in vivo experiments in lung and plasma cell tumor metastatic tumor systems, comparing the antitumor activity of the three enantiomeric preparations of 4-amino thalidomide. These data demonstrate that that the S(−) enantiomer was the most active enantiomer of 4-amino-thalidomide in each tumor model.

TABLE 1

| Tumor Model | Test Agent | Dose mg/kg/day | Activity |
|---|---|---|---|
| HsSultan B-cell lymphoma metastatic in SCID mice | Vehicle (0.5% methyl cellulose) | — | 26 days* |
| | R, S | 50 | 41 days* |
| | R(+) | 50 | 37 days* |
| | S(−) | 50 | 47 days* |
| HsSultan B-cell lymphoma metastatic in SCID mice | Vehicle (0.5% methyl cellulose) | — | 26 days* |
| | R, S | 200 | 28 days* |
| | R(+) | 200 | 31 days* |
| | S(−) | 200 | 47 days* |
| Lewis lung carcinoma metastatic in C57BL/6 mice | Vehicle (0.5% methyl cellulose) | — | 0.40 g # |
| | R, S | 100 | 0.27 g # |
| | R(+) | 100 | 0.42 g # |
| | S(−) | 100 | 0.17 g # |

*mean time to death
weight gain of lung

Example 9

Figure 2:
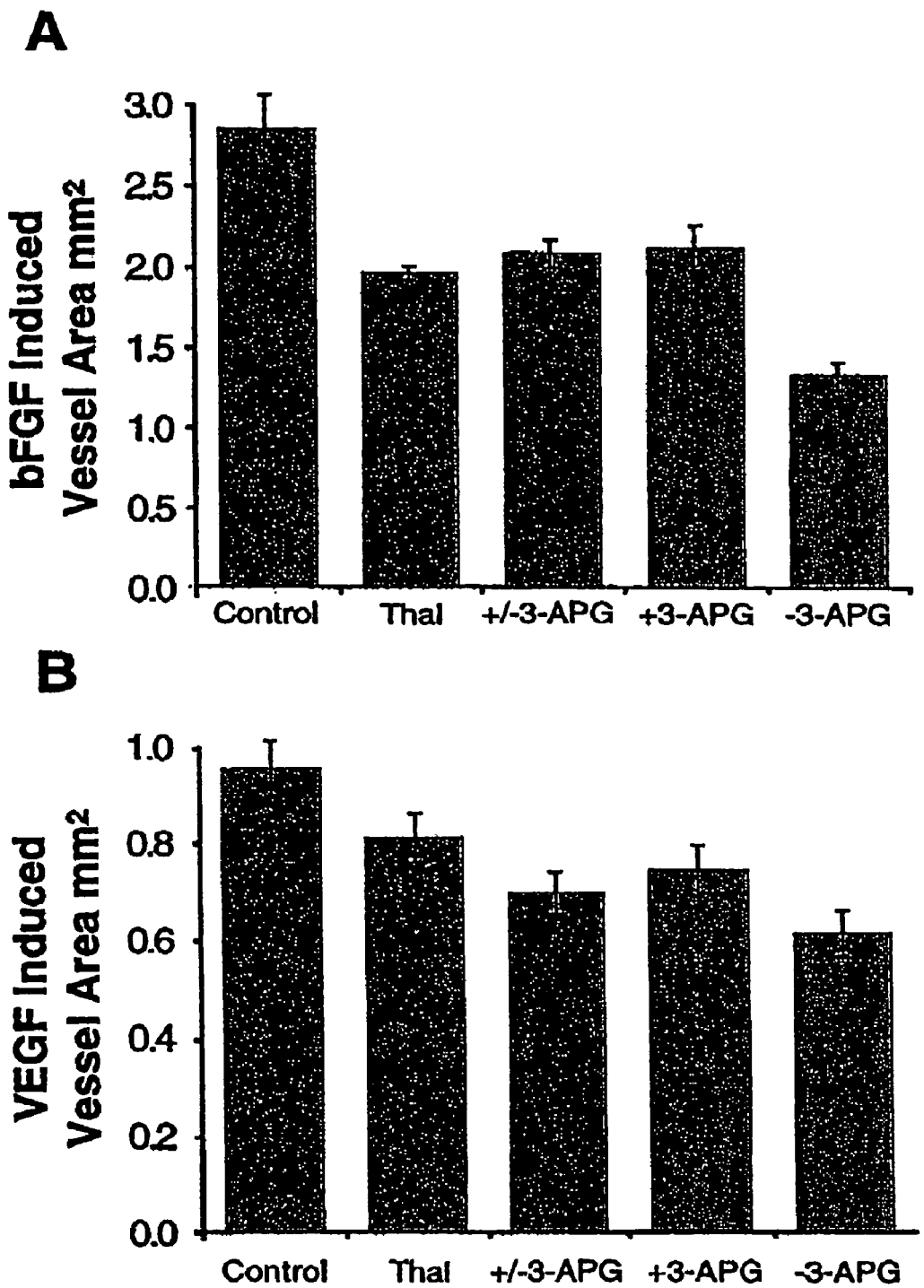
FIG. 2 illustrates the results of corneal micropocket assays employing the compounds of the present invention.

A corneal micropocket assay was performed as described in Kenyon, et al., A Model of Angiogenesis in the Mouse Cornea, *Invest. Ophtalmol. & Vis. Sci.*, 37, 1625-1632 (1996), which is incorporated herein in its entirety. Pellets were used containing 80 ng of bFGF or human recombinat VEGF (R&D Systems, Minneapolis, Minn.) in C57BL/6J mice. The treated groups received daily administration for five(bFGF) or six (VEGF consecutive days of thalidomide, S(−)- and R(+)-4-amino-thalidomide (3APG), S(−)3APG, and R(+)-3APG (50 mg/kg) suspended in 0.5% carboxymethylcellulose i.p. The area of vascular response was assessed on the fifth (bFGF) or sixth (VEGF) postoperative day using a slit lamp. The results are reported in FIG. 2. As indicated in FIG. 2, differences in bFGF induced neovascularization between S(−)-3APG and control were significant (n=9 each, P<0.0001) as were differences between S(−)-3 APG and thalidomide (n=9 each, P<0.01). Differences in VEGF induced neovascularization between S(−)-3APG and control were significant (n=9 each, P<0.001), as were differences between S(−)-3 APG and thalidomide (n=9 each, P<0.01).

By "an effective amount" is meant a therapeutically or prophylactically effective amount. Such amounts can be readily determined by an appropriately skilled person, taking into account the condition to be treated, the route of administration and other relevant factors. Such a person will readily be able to determine a suitable dose, mode and frequency of administration.

It should be understood, of course, tha the foregoing relates only to preferred embodiments of the present invention and that numerous modifications or alterations may be made therein without departing from the spirit and the scope of the invention as set forth in the appended claims.

What is claimed is:

1. A method of preparing S(−)-4-amino-thalidomide comprising:
    (a) contacting 3-nitrophthalic anhydride with S(−)-3-amino-glutarimide hydrobromide in the presence of acetic acid at a temperature of about 70° C. to about 80° C. to form S(−)-4-nitro-thalidomide; and
    (b) reducing the S(−)-4-nitro-thalidomide by hydrogenation to form S(−)-4-amino-thalidomide.

2. A method of preparing R(+)-4-amino-thalidomide comprising:
(a) contacting 3-nitrophthalic anhydride with R(+)-3-amino-glutarimide hydrobromide in the presence of acetic acid at a temperature of about 70° C. to about 80° C. to form R(+)-4-nitro-thalidomide; and
(b) reducing the R(+)-4-nitro-thalidomide by hydrogenation to form R(+)-4-amino-thalidomide.

3. The method of claim 1, wherein the contacting step occurs at about 70° C. to about 80° C. for about 18 to about 24 hours.

4. The method of claim 1, wherein the reducing step occurs in a mixture of dioxane and methanol.

* * * * *